United States Patent [19]

Richter et al.

[11] Patent Number: 5,747,508
[45] Date of Patent: May 5, 1998

[54] AMIDINOHYDRAZONES OF KETONES DERIVED FROM BENZO[B]FURAN, METHODS FOR THEIR PRODUCTION, AND PHARMACEUTICALS CONTAINING THESE COMPOUNDS

[75] Inventors: Peter Richter, Greifswald; Martin Elsner, Bielefeld; Barbara Vogt, Berlin, all of Germany

[73] Assignee: Helopharm G. Petrik GmbH, Berlin, Germany

[21] Appl. No.: 761,505

[22] Filed: Dec. 6, 1996

[30] Foreign Application Priority Data

Dec. 7, 1995 [DE] Germany ............ 195 47 263.2

[51] Int. Cl.$^6$ .............. A61K 31/34; C07D 307/81
[52] U.S. Cl. ............. 514/320; 514/401; 514/469; 546/196; 548/311.4; 549/467
[58] Field of Search ............. 549/467; 546/196; 548/311.4; 514/320, 401, 469

[56] References Cited

U.S. PATENT DOCUMENTS

| | | | |
|---|---|---|---|
| 3,248,401 | 4/1966 | Tondeur et al. | 549/468 |
| 3,931,157 | 1/1976 | Child et al. | 548/311.4 |
| 4,831,054 | 5/1989 | Levitt et al. | 514/469 |
| 5,278,169 | 1/1994 | Atwal et al. | 514/302 |

FOREIGN PATENT DOCUMENTS

| | | |
|---|---|---|
| 0281254 | 9/1988 | European Pat. Off. |
| 0286277 | 10/1988 | European Pat. Off. |
| 59-206378 | 11/1984 | Japan |
| 8807996 | 10/1988 | WIPO |
| 9109023 | 6/1991 | WIPO |
| 9504052 | 2/1995 | WIPO |

OTHER PUBLICATIONS

Misra et al., Potential Antiviral and Antituberculous Compounds, III. N-1-(4-Methoxy Napthylidene/2-benzofurylidene)-N-4-(aryl) Thiosemicarbazides . . .

Journal Für Praktische Chemie, (1967), Bd. 36, Nr. 5-6 pp. 260-264.

Ghelardoni et al., Isomeria geometrica in derivati del benzofurano 2-sostituiti, Gazzetta Chimica Italiana (1969), Bd. 99, Nr. 12 pp. 1273-1283.

Dann et al., Synthesen biskationischer, trypanocider 1-Benzofuran-Verbindungen, 13a and 13b, Liebigs Annalen Der Chemie, (Oct. 1982), Nr. 10 pp. 1836-1869.

Williams, E.M. Vaughan Ed., Antiarrhythmic Drugs, Table of Contents, 1989.

Chemical Abstracts, 102:113276, 1985 (Abstract of JP 59-206,378).

*Primary Examiner*—Fiona T. Powers
*Attorney, Agent, or Firm*—Webb Ziesenheim Bruening Logsdon Orkin & Hanson, P.C.

[57] ABSTRACT

This patent application describes new amidinohydrazones of ketones derived from benzo[b]furan having the general formula I

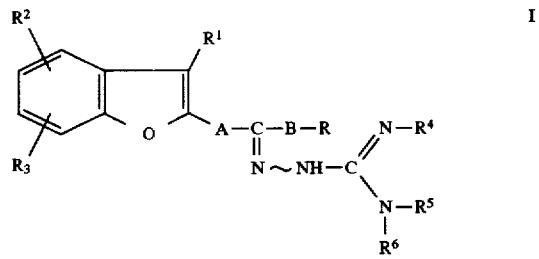

and their pharmaceutically acceptable salts, a method for their production, and pharmaceuticals containing these compounds.

The compounds described show improved effects of class III antiarrhythmic agents.

5 Claims, No Drawings

AMIDINOHYDRAZONES OF KETONES DERIVED FROM BENZO|B|FURAN, METHODS FOR THEIR PRODUCTION, AND PHARMACEUTICALS CONTAINING THESE COMPOUNDS

BACKGROUND OF THE INVENTION

1. Field of the Invention

This invention relates to new amidinohydrazones, methods for their production, and pharmaceuticals containing these compounds.

2. Prior Art

A number of compounds is applied in the treatment of cardiac arrhythmias that are quite diverse in their chemical structures and pharmacological effects. In 1970, Vaughan Williams proposed a classification system to differentiate between the various antiarrhythmic agents. This system is mainly based on the way in which the substances of the various classes affect ionic currents through membranes.

Class I compounds such as flecainide (INN), lidocaine (INN) and propafenon (INN) have a local anaesthetic effect on nervous and myocardial membranes by inhibiting the transmembrane inflow of sodium. They slow down conduction, which reduces the passing on of premature heartbeats. In addition, they suppress the tendency in damaged cells to send out premature heartbeats.

The class II compounds are the so-called β-blockers, for example, propranolol (INN).

β-Blockers have an antiarrhythmic effect in that they weaken or block adrenergic effects that interfere with the transmembrane ion currents.

The effect of class III antiarrhythmic agents is largely independent of an inhibition of the transmembrane sodium current. They have little or no influence on the resting potential of heart cells and on conduction. These compounds prolong the duration of the cardiac action potential and the refractory period, i.e. the period of time during which the heart cells cannot be excited. The underlying mechanism consists in influencing the repolarizing transmembrane outflow of potassium.

Cardioactive calcium antagonists such as verapamil (INN) or diltiazeme (INN) are called class IV antiarrhythmic agents. These compounds block the slow calcium inflow at the beginning of the excitation, thereby suppressing the formation and spread of so-called slow action potentials which may occur in the myocardium under specific pathological conditions.

With respect to the compounds of the invention, reference shall be made to class III antiarrhythmic agents.

Amiodarone (INN) and sotalol (INN) are considered to be prototypes of class III antiarrhythmic agents, although none of them is a "pure" member of this class. Sotalol has additional β-blocking properties, i.e. a class II effect, while amiodarone shows additional effects on sodium and calcium channels and, furthermore, has α- and β-adrenolytic effects. But these valuable properties of the two antiarrhythmic agents are accompanied by severe side effects which limit or even prohibit their application. These include gastrointestinal complaints such as nausea, vomiting, stomachache, constipation but also cerebral disturbances such as headache, drowsiness, visual disturbances, disturbed sleep, and dermatological problems such as hyperpigmentation of the skin and photosensitivity. The most severe and potentially lethal side effects are pulmonary fibrosis and liver impairments as well as proarrhythmic effects such as atrioventricular conduction block and torsade de pointes which necessitate treatment termination.

While benzo[b]furanyl ketones related to amiodarone have already been tested for their antiarrhythmic properties, amidinohydrazones of ketones derived from benzo|b|furan that have an antiarrhythmic effect have not been known as yet. The relevant literature only refers to 5-amidinobenzo[b]furan-2-carboxaldehyde amidinohydrazone dihydrochloride as being trypanocidal (Dann O., Char H., Greissmeier H.: Liebigs Ann. Chem 1982, 1836) as well as to bis-(7-hydroxybenzo[b]furan-2-yl) ketone amidinohydrazone hydrochloride (Kaken Pharm Co Ltd: JP 59 206 378) as being antiviral.

Thus there is an urgent need for novel substances with an antiarrhythmic effect.

SUMMARY OF THE INVENTION

It is an object of the present invention to provide compounds that comprise an improved efficacy/side effect ratio as compared with the class III antiarrhythmic agents available so far.

This problem is solved according to the invention by providing new amidinohydrazones of the general formula I

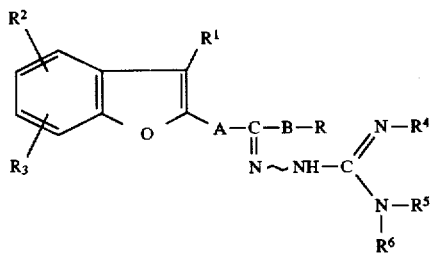

wherein

R is a linear or branched alkyl or dialkyl aminoethyl group containing up to 6 C atoms, or one of the residues

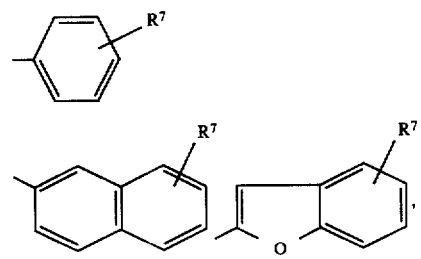

wherein $R^7$ represents a hydrogen atom, a halogen atom, a linear or branched alkyl or alkoxy group containing up to 6 C atoms, an aralkyl or aralkoxy group containing up to 9 C atoms, a cyano, nitro, methane sulfonamido, acetylamino, trifluoromethyl, trifluoromethoxy, amino, or (1H-imidazole-1-yl) group, A and B independently represent either $(CH2)_n$ or $(CH=CH)_m$, with n=0, 1 or 2 and m=0 or 1, $R^1$ is a hydrogen atom, an amino, a linear or branched alkyl residue containing up to 6 C atoms, an aralkyl residue containing up to 9 C atoms, a methane sulfonamido, acetylamino, cyano, (1H-imidazole-1-yl) residue, or one of the residues

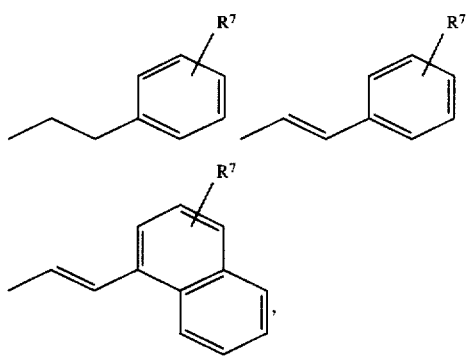

wherein

R⁷ is as defined above,

R² and R³ independently represent a hydrogen atom, a linear or branched alkyl or alkoxy group containing up to 6 C atoms, an aralkyl or aralkoxy group containing up to 9 C atoms, a halogen atom, a cyano, nitro, methane sulfonamido, acetylamino, trifluoromethyl, trifluoromethoxy, amino, or (1H-imidazole-1-yl) group, R⁴ is a hydrogen atom, a linear or branched alkyl group containing up to 6 C atoms, an aralkyl group containing up to 9 C atoms, or one of the residues

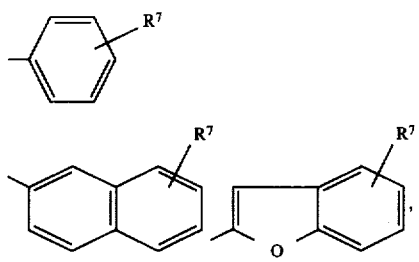

wherein

R⁷ is as defined above,

R⁵ and R⁶ independently represent a hydrogen atom, a linear or branched alkyl, alkanoyl or alkylsulfonyl residue containing up to 6 C atoms each, an aralkyl residue containing up to 9 C atoms, a (4-methylphenyl) sulfonyl, a trifluoroacetyl, or one of the residues

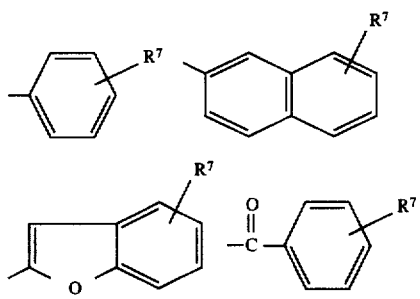

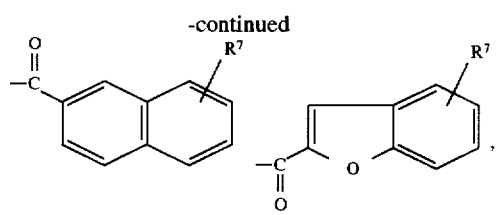

wherein

R⁷ is as defined above, or R⁴ and R⁵ jointly represent an ethylene or propylene fragment, or R⁵ and R⁶, together with the N atom, represent a piperidino, morpholino, or piperazino residue, and wherein the zig-zagged bond in the structure of amidinohydrazone indicates that the compounds are present in the form of (Z) or (E) isomers, or mixtures of isomers, as well as their salts formed with one or several physiologically tolerable acids such as mineral acids, linear or branched alkanoic or alkanoic acids or alkylsulfonic acids containing up to 6 C atoms or arenocarboxylic acids, the organic acids optionally carrying additional halogen, amino, dialkylamino (containing up to 6 C atoms), hydroxy, and carboxy residues.

DETAILED DESCRIPTION OF THE INVENTION

The present invention includes amidinohydrazones of the general formula I,

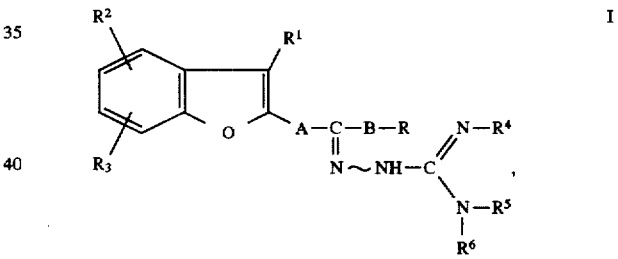

wherein

R is a linear or branched alkyl or dialkyl aminoethyl group containing up to 6 C atoms, or one of the residues

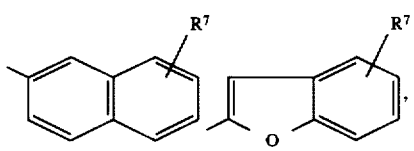

wherein

R⁷ represents a hydrogen atom, a halogen atom, a linear or branched alkyl or alkoxy group containing up to 6 C atoms, an aralkyl or aralkoxy group containing up to 9 C atoms, a cyano, nitro, methane sulfonamido, acetylamino, trifluoromethyl, trifluoromethoxy, amino, or (1H-imidazole-1-yl) group, A and B independently represent either $(CH_2)_n$ or $(CH=CH)_m$, with n=0, 1 or 2 and m=0 or 1, $R^1$ is a hydrogen atom, an amino, a linear or branched alkyl residue containing up to 6 C atoms, an aralkyl residue containing up to 9 C atoms, a methane sulfonamido, acetylamino, cyano, (1H-imidazole-1-yl) residue, or one of the residues

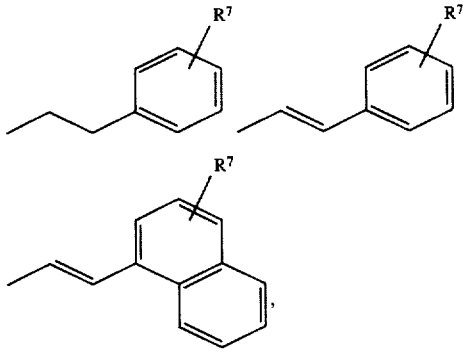

wherein $R^7$ is as defined above.

$R^2$ and $R^3$ independently represent a hydrogen atom, a linear or branched alkyl or alkoxy group containing up to 6 C atoms, an aralkyl or aralkoxy group containing up to 9 C atoms, a halogen atom, a cyano, nitro, methane sulfonamido, acetylamino, trifluoromethyl, trifluoromethoxy, amino or (1H-imidazole-1-yl) group, $R^4$ is a hydrogen atom, a linear or branched alkyl group containing up to 6 C atoms, an aralkyl group containing up to 9 C atoms, or one of the residues

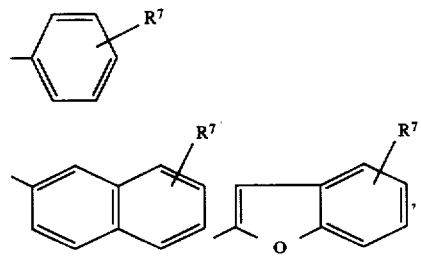

wherein $R^7$ is as defined above.

$R^5$ and $R^6$ independently represent a hydrogen atom, a linear or branched alkyl, alkanoyl, or alkylsulfonyl residue containing up to 6 C atoms, an aralkyl residue containing up to 9 C atoms, a (4-methylphenyl) sulfonyl, a trifluoroacetyl, or one of the residues

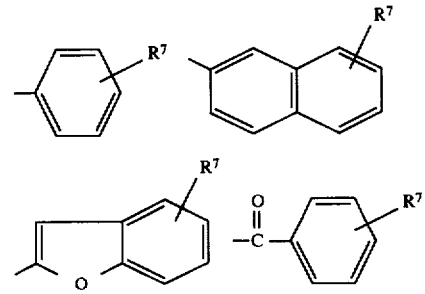

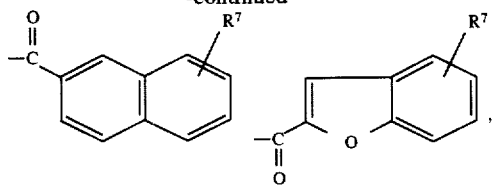

wherein $R^7$ is as defined above, or $R^4$ and $R^5$ jointly represent an ethylene or propylene fragment, or $R^5$ and $R^6$, together with the N atom, represent a piperidino, morpholino, or piperazino residue, and wherein the zig-zagged bond in the structure of amidinohydrazone indicates that the compounds are present in the form of (Z) or (E) isomers, or mixtures of isomers, as well as their salts formed with one or several physiologically tolerable acids such as mineral acids, linear or branched alkanoic or alkanoic acids or alkylsulfonic acids containing up to 6 C atoms or arenocarboxylic acids, the organic acids optionally carrying additional halogen, amino, dialkylamino (containing up to 6 C atoms), hydroxy, and carboxy residues.

Such compounds are preferred in which A and B are not present, and R is phenyl, 2-benzo[b]furanyl or 2-naphthyl replaced by $R^7$, the latter representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl).

Preferred are compounds in which $R^4$, $R^5$, and $R^6$ simultaneously represent hydrogen.

Also preferred are compounds in which $R^4$ and $R^5$ simultaneously represent hydrogen and $R^6$ represents n-alkyl, branched alkyl, aralkyl, n-alkylsulfonyl, branched alkylsulfonyl, n-alkanoyl, branched alkanoyl, (4-methylphenyl)sulfonyl, trifluoroacetyl, phenyl, 2-benzo[b]furanyl or 2-naphthyl optionally replaced by $R^7$ representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl). Furthermore, such compounds are preferred here in which $R^4$ is hydrogen, and $R^5$ and $R^6$ simultaneously represent n-alkyl, branched alkyl, aralkyl or, together with the nitrogen atom that carries them, represent piperidino, morpholino or piperazino•HX. Moreover, such compounds are preferred here in which $R^4$ and $R^5$ together represent an ethylene or propylene group, and $R^6$ represents hydrogen.

In addition, compounds are preferred in which $R^4$ and $R^5$ are hydrogen, $R^6$ is benzoyl, 2-benzo[b]furanoyl or 2-naphthoyl, and in which $R^7$ represents hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl).

Preferred are compounds in which A is not present, B is an ethenyl group (m=1), and R is phenyl, 2-benzo[b]furanyl or 2-naphthyl replaced by $R^7$ representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl). Particularly preferred are compounds in which $R^4$, $R^5$, and $R^6$ simultaneously represent hydrogen.

Preferred are compounds in which B is not present, A is an ethenyl group (m=1), and R is phenyl, 2-benzo[b]furanyl or 2-naphthyl replaced by $R^7$ representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl). Particularly preferred are compounds in which $R^4$, $R^5$, and $R^6$ simultaneously represent hydrogen.

Also preferred are compounds in which A is not present, B represents one or two methylene groups (n=1, 2), and R is phenyl, 2-benzo[b]furanyl, or 2-naphthyl replaced by $R^7$ representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl). Particularly preferred are compounds in which $R^4$, $R^5$, and $R^6$ simultaneously represent hydrogen.

Furthermore, compounds are preferred in which B is not present and A represents one or two methylene groups (n=1, 2), and R is phenyl, 2-benzo[b]furanyl, or 2-naphthyl replaced by $R^7$ representing hydrogen, n-alkyl, branched alkyl, aralkyl, alkoxy, aralkoxy, halogen, cyanogen, nitro, methane sulfonamido, acetylamino, trifluoromethyl, trifluoromethoxy, amine•HX or (1H-imidazole-1-yl). Particularly preferred are compounds in which $R^4$, $R^5$, and $R^6$ simultaneously represent hydrogen.

Particularly preferred are compounds which are present in the form of a pure (Z) isomer.

Particularly preferred are compounds which are present in the form of a pure (E) isomer.

The following compounds are preferred in particular:

(E)-2-benzoylbenzo[b]furan amidinohydrazone hydrochloride 39

(Z)-2-benzoylbenzo[b]furan amidinohydrazone hydrochloride 40

(Z/E)-2-benzoylbenzo[b]furan amidinohydrazone hydrochloride 39/40

(Z/E)-2-(4-methylbenzoyl)benzo[b]furan amidinohydrazone hydrochloride 41

(Z/E)-2-(4-methoxybenzoyl)benzo[b]furan amidinohydrazone hydrochloride 42

(Z/E)-2-(4-methane sulfonamidobenzoyl)benzo[b]furan amidinohydrazone hydrate hydrochloride 43

(Z/E)-2-(4-aminobenzoyl)benzo[b]furan amidinohydrazone dihydrochloride 44

(Z/E)-2-(4-bromobenzoyl)benzo[b]furan amidinohydrazone hydrochloride 45

(Z/E)-2-(4-chlorobenzoyl)benzo[b]furan amidinohydrazone hydrochloride 46

(Z/E)-2-(4-nitrobenzoyl)benzo[b]furan amidinohydrazone hydrochloride 47

(Z/E)-2-(4-cyanobenzoyl)benzo[b]furan amidinohydrazone hydrochloride 48

(Z/E)-5-bromo-2-(4-cyclohexylbenzoyl)benzo[b]furan amidinohydrazone hydrochloride 49

(Z/E)-2-(3-nitrobenzoyl)benzo[b]furan amidinohydrazone hydrochloride 50

(Z/E)-2-benzoyl-5-bromobenzo[b]furan amidinohydrazone hydrochloride 51

(Z/E)-5-bromo-2-(4-chlorobenzoyl)benzo[b]furan amidinohydrazone hydrochloride 52

(Z/E)-5-bromo-2-(4-bromobenzoyl)benzo[b]furan amidinohydrazone hydrochloride 53

(Z/E)-5-bromo-2-(4-cyanobenzoyl)benzo[b]furan amidinohydrazone hydrochloride 54

(Z/E)-2-(4-acetylaminobenzoyl)-5-bromobenzo[b]furan amidinohydrazone hydrochloride 55

(Z/E)-2-benzoyl-5-nitrobenzo[b]furan amidinohydrazone hydrochloride 56

(Z/E)-2-benzoyl-5-methylsulfonylaminobenzo[b]furan amidinohydrazone hydrochloride 57

(Z/E)-5-bromo-2-(4-nitrobenzoyl)benzo[b]furan amidinohydrazone hydrochloride 58

(Z/E)-2-(4-cyanobenzoyl)-5-nitrobenzo[b]furan amidinohydrazone hydrochloride 59

(Z/E)-2-benzoyl-5-cyanobenzo[b]furan amidinohydrazone hydrochloride 60

(Z/E)-5-bromo-2-(3-nitrobenzoyl)benzo[b]furan amidinohydrazone hydrochloride 61

(Z/E)-2-benzoyl-5,7-diiodobenzo[b]furan amidinohydrazone hydrochloride 62

(Z/E)-2-benzoyl-5,7-dibromobenzo[b]furan amidinohydrazone hydrochloride 63

(Z/E)-5-bromo-2-(4-methylbenzoyl)benzo[b]furan amidinohydrazone hydrochloride 64

(Z/E)-2-(4-fluorobenzoyl)benzo[b]furan amidinohydrazone hydrochloride 65

(Z/E)-2-(3,4-dimethoxybenzoyl)benzo[b]furan amidinohydrazone hydrochloride 66

(Z/E)-2-(2-fluorobenzoyl)benzo[b]furan amidinohydrazone hydrochloride 67

(Z/E)-2-(4-trifluoromethoxybenzoyl)benzo[b]furan amidinohydrazone hydrochloride 68

(Z/E)-2-(4-trifluoromethylbenzoyl)benzo[b]furan amidinohydrazone hydrochloride 69

(Z/E)-2-(3-trifluoromethoxybenzoyl)benzo[b]furan amidinohydrazone hydrochloride 70

(Z/E)-2-(3-trifluoromethylbenzoyl)benzo[b]furan amidinohydrazone hydrochloride 71

(Z/E)-5,7-diiodo-2-(4-trifluoromethylbenzoyl)-benzo[b]furan amidinohydrazone hydrochloride 72

(Z/E)-5-nitro-2-(3-trifluoromethoxybenzoyl)benzo[b]furan amidinohydrazone hydrochloride 73

(Z/E)-5-chloro-2-(4-trifluoromethylbenzoyl)benzo[b]furan amidinohydrazone hydrochloride 74

(Z/E)-5-nitro-2-(4-trifluoromethylbenzoyl)benzo[b]furan amidinohydrazone hydrochloride 75

(Z/E)-5-nitro-2-(4-trifluoromethoxybenzoyl)benzo[b]furan amidinohydrazone hydrochloride 76

(Z/E)-5-nitro-2-(3-trifluoromethylbenzoyl)benzo[b]furan amidinohydrazone hydrochloride 77

(Z/E)-2-benzoyl-5-chlorobenzo[b]furan amidinohydrazone hydrochloride 78

(Z/E)-2-benzoyl-7-methoxybenzo[b]furan amidinohydrazone hydrochloride 79

(Z/E)-5-methylsulfonylamino-2-(3-trifluoromethylbenzoyl)-benzo[b]furan amidinohydrazone hydrochloride 80

(Z/E)-1-(benzo[b]furan-2-yl)-3-(4-methylsulfonylaminophenyl)prop-2-ene-1-one amidinohydrazone hydrochloride 81

(Z/E)-1-(benzo[b]furan-2-yl)-3-phenylprop-2-ene-1-one amidinohydrazone hydrochloride 82

(Z/E)-1-(benzo[b]furan-2-yl)-3-(4-fluorophenyl)prop-2-ene-1-one amidinohydrazone hydrochloride 83

(Z/E)-1-(benzo[b]furan-2-yl)-3-(4-chlorophenyl)prop-2-ene-1-one amidinohydrazone hydrochloride 84

(Z/E)-1-(benzo[b]furan-2-yl)-3-(4-nitrophenyl)prop-2-ene-1-one amidinohydrazone hydrochloride 85

(Z/E)-1-(benzo[b]furan-2-yl)-3-(4-methoxyphenyl)prop-2-ene-1-one amidinohydrazone hydrochloride 86

(Z/E)-1-(benzo[b]furan-2-yl)-3-(3-bromphenyl)prop-2-ene-1-one amidinohydrazone hydrochloride 87

(Z/E)-1-(benzo[b]furan-2-yl)-3-(3-nitrophenyl)prop-2-ene-1-one amidinohydrazone hydrochloride 88

(Z/E)-1-(benzo[b]furan-2-yl)-3-(4-trifluoromethylphenyl) prop-2-ene-1-one amidinohydrazone hydrochloride 89

(Z/E)-1-(benzo[b]furan-2-yl)-3-phenylpropan-1-one amidinohydrazone hydrochloride 90

(Z/E)-1-(benzo[b]furan-2-yl)-3-(4-chlorophenyl)propan-1-one amidinohydrazone hydrochloride 91

(Z/E)-1-(benzo[b]furan-2-yl)-3-(4-methoxyphenyl) propan-1-one amidinohydrazone hydrochloride 92

(Z/E)-1-(benzo[b]furan-2-yl)-3-(3-methylsulfonylaminophenyl) propan-1-one amidinohydrazone hydrochloride 93

(Z/E)-3-(benzo[b]furan-2-yl)-1-phenylprop-2-ene-1-one amidinohydrazone hydrochloride 94

(Z/E)-3-(benzo[b]furan-2-yl)-1-(3-methylsulfonylaminophenyl) prop-2-ene-1-one amidinohydrazone hydrochloride 95

(Z/E)-3-(benzo[b]furan-2-yl)-1-(4-methylsulfonylaminophenyl) prop-2-ene-1-one amidinohydrazone hydrochloride 96

(Z/E)-3-(benzo[b]furan-2-yl)-1-(3-methylsulfonylaminophenyl) propan-1-one amidinohydrazone hydrochloride 97

(Z/E)-3-(benzo[b]furan-2-yl)-;-(4-methylsulfonylaminophenyl) propan-1-one amidinohydrazone hydrochloride 98

(Z/E)-2-benzoylbenzo[b]furan-$N^3,N^3$-dimethyl amidinohydrazone hydrochloride 99

(Z/E)-2-benzoylbenzo[b]furan-$N^3$-phenyl-amidinohydrazonium nitrate 100

(Z/E)-2-benzo[b]furan-(4-methansulfonamidobenzoyl)-$N^3$-phenyl amidinohydrazonium nitrate 101

(Z/E)-2-benzoylbenzo[b]furan-$N^3$-(pentamethylene) amidinohydrazone hydrochloride 102

(Z/E)-2-benzoylbenzo[b]furan-$N^3$-prop-2-yl-amidinohydrazone hydroiodide 103

Bis-(benzo[b]furan-2-yl) ketone amidinohydrazone hydrochloride 104

(Z/E)-(5-bromobenzo[b]furan-2-yl) (naphth-2-yl) ketone amidinohydrazone hydrochloride 105

(Z/E)-(benzo[b]furan-2-yl) (5-bromobenzo[b]furan-2-yl) ketone amidinohydrazone hydrochloride 106

(Z/E)-1-(benzo[b]furan-2-yl)-3-dimethylaminopropane-1-one amidinohydrazone hydrochloride 107

(Z/E)-2-acetylbenzo[b]furan amidinohydrazone hydrochloride 108

(Z/E)-benzo[b]furan-2-yl)(5,7-dibromobenzo[b]furan-2-yl) ketone amidinohydrazone hydrochloride 109

(Z/E)-1-(5-bromobenzo[b]furan-2-yl)propane-1-one amidinohydrazone hydrochloride 110

(Z/E)-2-phenylacetylbenzo[b]furan amidinohydrazone hydrochloride 111

(Z/E)-5-chloro-2-phenylacetylbenzo[b]furan amidinohydrazone hydrochloride 112

(Z/E)-5-bromo-2-phenylacetylbenzo[b]furan amidinohydrazone hydrochloride 113

(Z/E)-1-(benzo[b]furan-2-yl)propane-1-one amidinohydrazone hydrochloride 114

(Z/E)-2-benzoylbenzo[b]furan-$N^2$-(imida-zoline 2 yl)hydrazone hydrochloride 115

(Z/E)-2-benzoyl-5,7-dibromobenzo[b]furan-$N^2$-(imidazoline-2-yl) hydrazone hydrochloride 116

(Z/E)-3-amino-2-benzoyl-benzo[b]furan amidinohydrazone hydrochloride hydrate 117

(Z/E)-2-benzoyl-3-methylbenzo[b]furan amidinohydrazone hydrochloride 118

(Z/E)-2-benzoyl-5-benzyloxy-3-phenethylbenzo[b]furan amidinohydrazone hydrochloride 119

(Z/E)-2-benzoyl-7-benzyloxy-3-methylbenzo[b]furan amidinohydrazone hydrochloride 120

(Z/E)-2-benzoyl-3-(2-(naphth-1-yl)ethene-1-yl) benzo[b]furan amidinohydrazone hydrochloride 121

(Z/E)-2-benzoyl-7-benzyloxy-3-phenethylbenzo[b]furan amidinohydrazone hydrochloride 122

(Z/E)-2-benzoyl-3-methyl-5-nitrobenzo[b]furan amidinohydrazone hydrochloride 123

(Z/E)-2-benzoylbenzo[b]furan-$N^3$-benzoyl amidinohydrazone hydrochloride 124

(Z/E)-2-benzoylbenzo[b]furan-$N^3$-(4-methylsulfonylamino-benzoyl) amidinohydrazone hydrochloride 125

(Z/E)-2-benzoylbenzo[b]furan-$N^3$-(4-nitrobenzoyl) amidinohydrazone hydrochloride 126

(Z/E)-2-benzoyl-5-bromobenzo[b]furan-$N^3$-benzoyl amidinohydrazone hydrochloride 127

(Z/E)-2-benzoyl-5,7-dibromobenzo[b]furan-$N^3$-benzoyl amidinohydrazone hydrochloride 128

Furthermore, this invention relates to a method for producing the amidinohydrazones according to the invention of the general formula I, characterized in that ketones derived from benzo[b]furan of the general formula

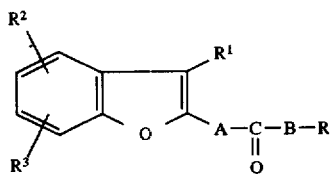

II in which the residues R, $R^1$, $R^2$, and $R^3$ are as defined above, are fused together in a generally known way by heating in a short-chain alkanol in the presence of mineral or sulfonic acids with an aminoguanidine of the general formula III,

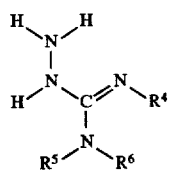

III in which the residues $R^4$, $R^5$, and $R^6$ are as defined above, said aminoguanidine optionally being present in the form of a salt formed with an inorganic or organic acid, and, optionally, by releasing the base from the compounds thus obtained and reacting said base with one or several physiologically tolerable acids such as mineral acids, linear or branched alkanoic or alkanoic acids or alkylsulfonic acids containing up to 6 C atoms or arenocarboxylic acids, the organic acids optionally carrying an additional halogen, amino, dialkylamino (containing up to 6 C atoms), hydroxy, and carboxy residue, and by converting them into a physiologically tolerable salt, or is reacted in a suitable solvent, e.g. pyridine, and in the presence of auxiliary bases with acyl halogenides of the formulae

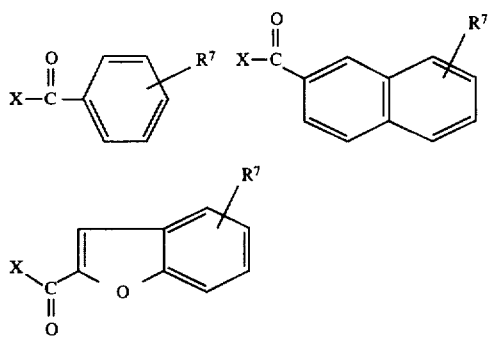

in which $R^7$ is as defined above and X represents a halogen atom, and by reacting the N acyl derivatives obtained with one or several physiologically tolerable acids such as mineral acids, linear or branched alkanoic or alkanoic acids or alkylsulfonic acids containing up to 6 C atoms or arenocarboxylic acids, the organic acids optionally being replaced by halogen, amino, dialkylamino (containing up to 6 C atoms), hydroxy, and carboxy residues, and by converting them into a physiologically tolerable salt.

Chart A gives a survey of the preparation of the amidinohydrazones of the invention. The substituted ketones below were prepared as follows:

2-benzoylbenzo[b]furan: Rap, E.: Gazz. Chim. Ital. 25, 285 (1895); Schraufstätter, E.; Deutsch, D.: Z. Naturforsch. 46, 276 (1949); Sen, A. B.; Saxena, M. S.: J. Indian Chem. Soc. 34, 136 (1958); Ghelardoni, M.; Pestellini, V.; Musante, C.: Gazz. Chim. Ital. 99, 1273 (1969);

2-(4-methoxybenzoyl) benzo[b]furan and 2-(4-methylbenzoyl) benzo[b]furan: Buu Hoï, N. P.; Bisagni, E.; Royer, R.: J. Chem. Soc. 1957, 625;

2-(4-chlorobenzoyl)benzo[b]furan and 2-(4-bromobenzoyl)-benzo[b]furan: ibid., Ghelardoni, M.; Pestellini, V.; Musante, C.: Gazz. Chim. Ital. 99, 1273 (1969);

2-(4-nitrobenzoyl)benzo[b]furan: Ghelardoni, M.; Fedi, M.; Russo, F.: Ann. di Chim. 52, 29 (1962);

5-bromo-2-(4-brombenzoyl)benzo[b]furan: Schraufstätter, E.; Deutsch, D.: Z. Naturforsch. 46, 276 (1949); 2-(3-dimethylaminopropionyl)benzo[b]furan: Knott, E. B.: J. chem. Soc. 1947, 1190.

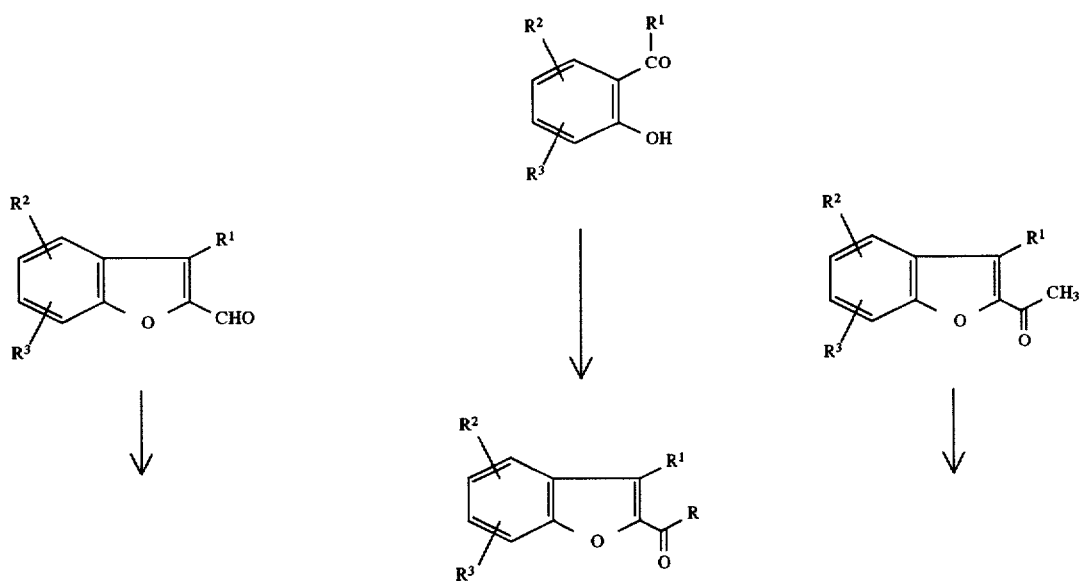

Chart A

-continued
Chart A

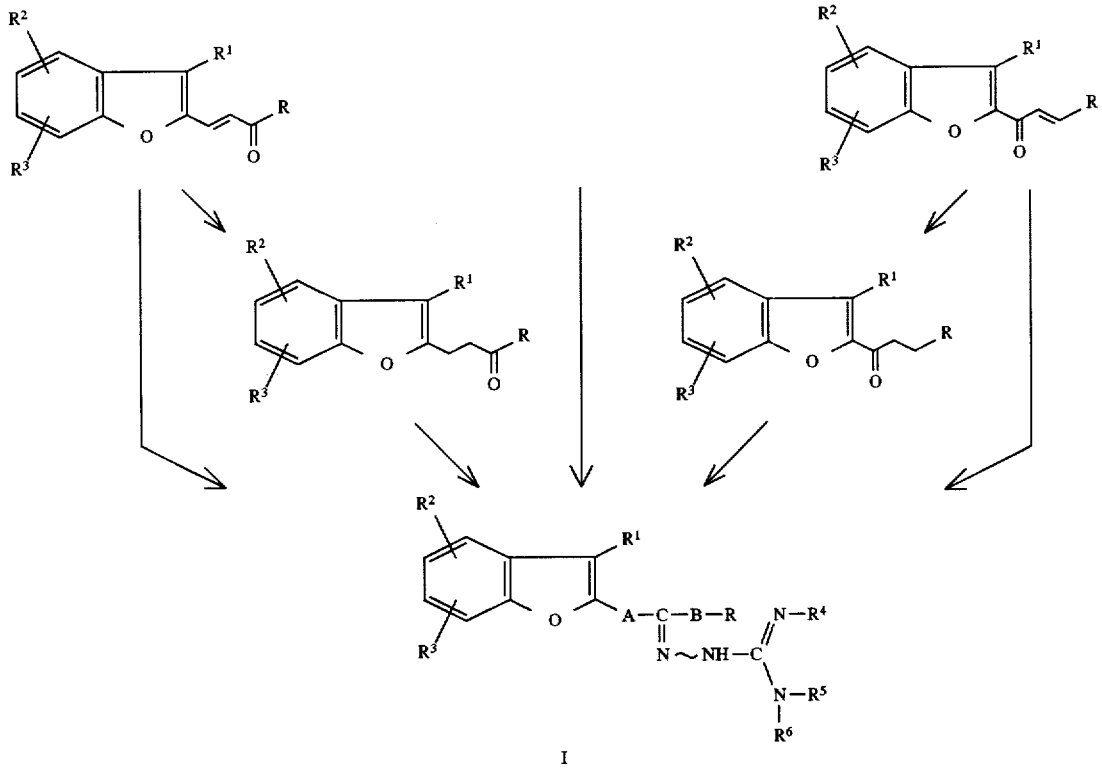

In the above chart, R, $R^1$, $R^2$, $R^3$, $R^4$, $R^5$, $R^6$, A, and B are as defined above.

The mixtures of isomers obtained after condensation are split up into the pure (Z) or (E) isomers of the compounds of the general formula I using methods known to an expert skilled in the art, for example, fractional crystallization.

The salts obtained during condensation are, for example, converted into their underlying bases using alkali hydroxide solutions, and said bases are reacted with the respective acids to yield salts of the general formula I that are physiologically and/or pharmaceutically more acceptable. The bases can optionally be released in a solvent such as pyridine and in the presence of auxiliary bases.

Common physiologically tolerable inorganic and organic acids include the following: hydrochloric acid, hydrobromic acid, phosphoric acid, sulfuric acid, oxal acid, maleic acid, fumaric acid, lactic acid, acetic acid, tartaric acid, malic acid, citric acid, salicylic acid, adipic acid, and benzoic acid. Other acids that can be used are described, for example, in *Fortschritte der Arzneimittelforschung*, Vol. 10, pages 224–225, Birkhäuser Verlag, Basel and Stuttgart, 1966, and in *Journal of Pharmaceutical Sciences*, Vol. 66, pages 1–5 (1977).

Acid addition salts are normally obtained in a generally known way by mixing the free base or its solutions with the respective acid or its solutions in an organic solvent, for example, a lower alcohol such as methanol, ethanol, n-propanol or isopropanol, or a lower ketone such as acetone, methyl ethyl ketone or methyl isobutyl ketone, or an ether such as diethyl ether, tetrahydrofurane or dioxane. Compositions of the above-mentioned solvents may be used for improved crystallizing. In addition, physiologically compatible hydrous solutions of acid addition salts of the compound according to formula I may be produced in a hydrous acidic solution.

The acid addition salts of compounds of the general formula I can be converted into a free base in a generally known way, e.g. using alkalis or ion exchangers. Other salts can be obtained by reacting this free base with inorganic or organic acids, especially acids suited for forming pharmaceutically acceptable salts. These and other salts of the new compound, such as its picrate, may be used to purify the free base: the free base is converted into a salt, the salt is separated, and the base is once again released from the salt.

Another object of this invention are pharmaceuticals designed for oral, rectal, subcutaneous, percutaneous, local, transcutaneous, cutaneous, intravenous or intramuscular applications that contain as an active ingredient, apart from the usual substrates and diluents, at least one compound of the general formula I or its acid addition salt.

Apart from the ingredients mentioned above, the pharmaceuticals of the invention may contain other active agents mainly selected from classes I, II, III and/or IV of antiarrhythmic agents. Class I antiarrhythmic agents are, for example, flecainide, lidocaine, propafenone; class II antiarrhythmic agents are, for example, propranolol, oxprenolol, practolol, acebutolol, pindolol, metindol, nadolol, labetalol, bisoprolol, tolamolol, formoterol, celiprolol, bunitrolol, atenolol, metoprolol; class III antiarrhythmic agents are, for example, amiodarone and sotalol, and class IV antiarrhythmic agents are, for example, verapamil or diltiazem.

The pharmaceuticals of the invention are produced in a known way using the usual solid or liquid substrates or diluents and the common adjuvants used in pharmaceutical engineering and with an appropriate dosage depending on the intended mode of application. Preferred formulations are those forms suitable for oral administration, for example, tablets, film tablets, dragées, capsules, pills, powder, solutions, suspensions, or depot forms.

Consideration may also be given to parenteral formulations such as injection solutions. Suppositories represent another form of application.

Tablets may be obtained, for example, by intermixing the active substance with known adjuvants, for example, inert diluents such as dextrose, sugar, sorbitol, mannite, polyvinylpyrrolidone, blasting agents such as maize starch or alginic acid, binders such as starch or gelatine, lubricants such as magnesium stearate or talcum and/or materials by which to produce a depot effect such as carboxyl polymethylene, carboxymethyl cellulose, cellulose acetate phthalate or polyvinyl acetate. Tablets may consist of several layers.

Dragées may be produced accordingly by coating cores manufactured in analogy to tablet manufacture using agents generally applied to dragées coating, for example, polyvinylpyrrolidone or shellac, Arabic gum, talcum, titanium dioxide, or sugar. The coating of the dragées may also consist of several layers in which the adjuvants mentioned in the paragraph on tablets can be used.

Solutions or suspensions containing the active agent of the invention may additionally contain flavour-enhancing substances such as saccharin, cyclamate or sugar, or aromatic substances such as vanillin or orange extract. They may also contain suspension-supporting adjuvants such as sodium carboxymethyl cellulose, or preservatives such as p-hydroxybenzoates. Capsules containing active substances may be produced, for example, by mixing the active substance with an inert substrate such as lactose or sorbitol, and encapsulating such mixture in gelatine capsules.

Appropriate preparations for percutaneous, local, cutaneous, or transcutaneous administration may be produced by mixing the compounds of the invention with substrates and adjuvants known to an expert skilled in the art using methods known to an expert skilled in the art.

Appropriate suppositories may be made by mixing the active substance with the suitable substrates such as neutral fats or polyethylene glycol and their derivatives.

The amidinohydrazones of the invention have an antiarrhythmic effect that is produced by prolongation of the cardiac action potential duration accompanied by an extension of the refractory period. Thus these compounds should be classified as class III antiarrhythmic agents. They can best be used for the treatment and prevention of ventricular and supraventricular arrhythmias that are based on a re-entry mechanism; in particular, they are used in cases of chronic tachyarrhythmias.

The cardioactive effect of the substances of the invention is a prolongation of the repolarization phase (i.e. the duration of the action potential or the Q-T interval in an ECG), which is a class III activity according to the classification of antiarrhythmic agents based on Vaughan Williams. Class III antiarrhythmic agents are especially suited for treating life-threatening cardiac arrhythmias because they neither influence the excitability of the heart cells nor conduction within the heart. Class III antiarrhythmic agents cause a prolongation of the action potential duration and thus increase the refractory period of the myocardium by an effect on the repolarizing potassium channels. The prolongation of the refractory period under the influence of these substances is accompanied by a reduced occurrence of critical re-entry arrhythmias. Re-entry arrhythmias are considered to be the main reason for ventricular fibrillation, an arrhythmia that causes sudden cardiac death.

Antiarrhythmic properties can be studied in vitro and in vivo using various experimental models. Among the appropriate methods are electrophysiological examinations of isolated myocardial preparations, e.g. Purkinje fibre, papillary muscle, atrial and ventricular tissue of guinea pigs, rats, rabbits, or dogs. The action of the compounds of the invention on both the resting and the action potential is studied in comparison with a placebo and a reference substance. Dogs or pigs are frequently used for in vivo tests as these experimental animals have been studied best so that a great amount of comparative data is available. The compounds to be tested are administered to animals showing the arrhythmias after a myocardial infarction was induced in them in an appropriate way. These tests can either be made under anaesthesia by triggering the tachycardiac re-entry arrhythmias by means of programmed ventricular stimulation, or using the test model of sudden cardiac death in unanaesthetised dogs where the animals are subjected to an acute ischaemia under a physical strain. More than 90% of all untreated animals develop ventricular fibrillation.

The following test results prove the antiarrhythmic effectivity of the amidinohydrazones of ketones derived from benzo[b]furan.

A specific test model was developed as a large range of the desired electrophysiological properties and the progress of the desired effect over time are to be tested for the compounds under examination.

Guinea pigs having a body weight of approx. 300 g were used as experimental animals. Five animals were used for each substance. The animals were given equimolar doses of the substances according to the invention and a daily intraperitoneal injection of 80 mg/kg of amiodarone and placebo for reference over a period of seven days. ECG measurements were carried out on days 3, 5, and 7 to check the effect of the substances applied on the heart rate (R-R interval) and especially on the Q-T interval in the electrocardiogram (as a measure for excitation spread and repolarization). The animals were killed 24 hours after the last injection of the substance on day 8, and the papillary muscle was taken out of their hearts for electrophysiological examination.

Amiodarone was deliberately chosen as a reference substance as it is accepted as the most effective antiarrhythmic agent and does not show reverse use dependence, i.e. that the substance does not lose its prolonging effect on action potentials and refractory periods at high heart rates (i.e. short stimulation cycles).

TABLE 1

Qualitative ECG effects

| Compound | R-R interval | Q-T interval (frequency corrected) |
|---|---|---|
| Amiodarone | 0 | + |
| 101 | 0 | + |
| 106 | + | + |
| 126 | + | + |
| 127 | 0 | 0 |
| 128 | 0 | 0 |

+: significant prolongation ($p < 0.05$ compared with placebo)
0: no effect compared with placebo

TABLE 2

Qualitative effects on action potential

| Compound | MDP | APA | $V_{max}$ | $APD_{50}$ | $APD_{90}$ |
|---|---|---|---|---|---|
| Amiodarone | 0 | 0 | 0 | + | + |
| 101 | 0 | 0 | 0 | + | + |

TABLE 2-continued

Qualitative effects on action potential

| Compound | MDP | APA | $V_{max}$ | $APD_{50}$ | $APD_{90}$ |
|---|---|---|---|---|---|
| 106 | 0 | 0 | 0 | + | + |
| 126 | 0 | 0 | 0 | + | + |
| 127 | 0 | 0 | 0 | + | + |
| 128 | 0 | 0 | 0 | 0 | + |

+: significant prolongation ($p < 0.05$ compared with placebo)
0: no effect compared with placebo
APA = action potential amplitude,
$APD_{50}$ = action potential duration at 50% repolarization,
$APD_{90}$ = action potential duration at 90% repolarization,
MDP = maximum diastolic potential,
$V_{max}$ = maximum rate of rise of the action potential The effects that the compounds of the invention have on the relevant parameters of the ECG and the action potential are summarized in Tables 1 and 2 and compared with the results obtained for amiodarone. It should be emphasized here that the new compounds to be tested show the desired characteristics, that is, significant prolongation of action potential duration ($APD_{50}$ and $APD_{90}$) and of the Q-T interval. Like amiodarone and as desired the new substances do not influence the other parameters of the action potential, i. e. the maximum diastolic potential (MDP) which corresponds to the resting potential and controls the excitability of the heart cells, the maximum spread rate ($V_{max}$) of the action potential during electrical excitation and the action potential amplitude (APA) that are decisive for the propagation of excitation and the conduction velocity.

One of the most important benefits of amiodarone in comparison with sotalol and other class III antiarrhythmic agents under development is that it does not show reverse use dependence when it is applied chronically. This means that the desired effect, i.e. the prolongation of the action potential and of the refractory period, is reduced at high heart rates when there is a particular risk of life-threatening re-entry tachycardias in compromised hearts. It is therefore a requirement for research in this field to identify such compounds that do not show reverse use dependence. This requirement is met by the compounds of the invention.

Table 3 lists quantitative changes in individual electrophysiological parameters after chronic administration of one of the substances of the invention or chronic administration of amiodarone, respectively, in comparison with placebo. More specifically, it shows the percentage change in refractory periods (ERP) of the atrial and ventricular muscles in addition to the change in action potential duration (APD) in the papillary muscle at low (1000 ms) and high (300 ms) stimulation rates.

TABLE 3

Quantitative change in electrophysiological parameters

| | Amiodarone | 126 |
|---|---|---|
| $ERP_{papillary\ muscle}$ | +18.7%* | +19.6%* |
| $ERP_{left\ atrium}$ | +21.3%* | +24.0%* |
| $APD_{50}$ (1000 ms) | +11.5%* | +23.8%* |
| $APD_{90}$ (1000 ms) | +11.6%* | +21.8%* |
| $APD_{50}$ (300 ms) | +19.7%* | +28.4%* |
| $APD_{90}$ (300 ms) | +15.6%* | +19.3%* |

*significant compared with placebo with $p < 0.05$
ERP = effective refractory period (measured in papillary muscle or left atrium, respectively, at a stimulation cycle of 300 ms)
$APD_{50}$ (1000 ms) = $APD_{50}$ at a stimulation cycle of 1000 ms

TABLE 3-continued

Quantitative change in electrophysiological parameters

| | Amiodarone | 126 |
|---|---|---|

$APD_{50}$ (1000 ms) = $APD_{90}$ at a stimulation cycle of 1000 ms
$APD_{50}$ (300 ms) = $APD_{50}$ at a stimulation cycle of 300 ms
$APD_{90}$ (300 ms) = $APD_{90}$ at a stimulation cycle of 300 ms These results show that the compounds of the invention show a distinct class III activity which does not displace reverse use dependence, i.e. that their antiarrhythmic action to prolong repolarization is not lost at high heart rates and in states of tachycardia when they are most needed. The amidinohydrazones of the invention thus have effects that are at least equal, if not superior to those of amiodarone.

The following examples shall explain the invention:

EXAMPLE 1

2-benzoylbenzo[b]furan 1

24.4 g of salicylaldehyde and 300 ml of ethanol are mixed with 11.6 g of potassium hydroxide. The resulting suspension is agitated at room temperature until the potassium hydroxide is completely dissolved. Subsequently, 31 g of phenacyl chloride are added in portions to the solution, and the batch is heated under stirring in a reflux condenser for 2 hours. The crystals precipitated while cooling down to room temperature are filtered by suction, washed with water, and recrystallized from methanol. Another fraction may be obtained by evaporating the mother liquor. Yield: 70%, colourless crystals.

Melting range: 84°–86° C.

The compounds listed in Tables 4 and 5 are produced in a similar way.

TABLE 4

| Name | $R^2$ | $R^7$ | Yield [%] | Melting range [°C.] (recrystallized from) | Total formula (molar mass) |
|---|---|---|---|---|---|
| 2 | H | 4-cyclo-$C_6H_{11}$ | 77 | 105–109 (methanol) | $C_{21}H_{20}O_2$ (304.4) |
| 3 | H | 4-CN | 40 | 197–199 (methanol) | $C_{16}H_9NO_2$ (247.3) |
| 4 | H | 4-$CH_3SO_2NH$ | 95 | 143–146 (methanol) | $C_{16}H_{13}NO_4S$ (315.3) |
| 5 | $NO_2$ | H | 56 | 203–205 (n-propanol) | $C_{15}H_9NO_4$ (267.2) |
| 6 | Br | 4-$NO_2$ | 87 | 186–188 (n-propanol) | $C_{15}H_8BrNO_4$ (346.1) |
| 7 | Br | 4-CN | 30 | 195–198 (n-propanol) | $C_{16}H_8BrNO_2$ (326.2) |
| 8 | Br | 4-$CH_3CONH$ | 80 | 205–210 (n-propanol) | $C_{17}H_{12}BrNO_3$ (358.2) |
| 9 | $NO_2$ | 4-$NO_2$ | 55 | 204–210 (n-propanol) | $C_{15}H_8N_2O_6$ (312.2) |
| 10 | $NO_2$ | 4-CN | 57 | 197–202 dec. (n-propanol) | $C_{16}H_8N_2O_4$ (292.3) |
| 11 | $NO_2$ | 4-$CH_3CONH$ | 99 | 204–214 dec. (n-propanol) | $C_{17}H_{12}N_2O_5$ (324.2) |
| 12 | Br | 4-cyclo-$C_6H_{11}$ | 60 | 159–160 (n-propanol) | $C_{21}H_{19}BrO_2$ (383.1) |
| 13 | H | 4-F | 72 | 135–137 (n-propanol) | $C_{15}H_9FO_2$ (240.2) |

TABLE 4-continued

[Structure: R² substituted benzofuran linked via C=C to phenyl ring with R⁷ substituent, with C=O]

| Name | R² | R⁷ | Yield [%] | Melting range [°C.] (recrystallized from) | Total formula (molar mass) |
|---|---|---|---|---|---|
| 14 | H | 3,4-(CH₃O)₂ | 58 | 138–141 (n-propanol) | C₁₇H₁₄O₄ (282.3) |
| 15 | H | 2-F | 32 | 117–119 (methanol/ether) | C₁₅H₉FO₂ (240.2) | of concentrated hydrochloric acid. The batch is cooled after 10 h, and the precipitated yellow mass of crystals is filtered off by suction and rewashed with a small quantity of cold methanol.

Yield: 60%, yellow crystals

Melting range: 109°–111° C.

The compounds listed in Table 6 were prepared in accordance with analogous instructions. The substances thus obtained mostly are sufficiently pure. If required, they can be recrystallized from methanol or the like. The yields are between 50% and 97% of the theoretical quantity. Benzo[b]furan-2-carboxaldehydes and acetophenones, in whatever way substituted, can be condensed in a similar way and produce good yields as well.

TABLE 5

[Structure: R² substituted benzofuran with C(=O)R group]

| Name | R² | R | Yield [%] | Melting range [°C.] (recrystallized from) | Total formula (molar mass) |
|---|---|---|---|---|---|
| 16 | Br | [2-methylbenzofuran group] | 62 | 163–164 (n-propanol) | C₁₇H₉BrO₃ (341.2) |
| 17 | Br | [2-methylnaphthyl group] | 64 | 141–143 (n-propanol) | C₁₉H₁₁BrO₂ (351.2) |
| 18 | H | C₂H₅ | 51 | 52–53 (2-propanol) | C₁₁H₁₀O₂ (174.2) |
| 19 | Br | C₂H₅ | 43 | 87–91 (ethanol) | C₁₁H₉BrO₂ (253.1) |
| 20 | H | CH₂—C₆H₅ | 47 | 72–73 (ethanol) | C₁₆H₁₂O₂ (236.3) |
| 21 | Cl | CH₂—C₆H₅ | 40 | 99–100 (ethanol) | C₁₆H₁₁ClO₂ (238.7) |
| 22 | Br | CH₂—C₆H₅ | 41 | 105–106 (ethanol) | C₁₆H₁₁BrO₂ (315.2) |

EXAMPLE 2

1-(benzo[b]furan-2-yl)-3-phenylprop-2-ene-1-one 23

8 g of 2-acetyl benzo[b]furan and 6 g of benzaldehyde are heated to boiling in 50 ml of methanol in the presence of 3

TABLE 6

[Structure: benzofuran-2-yl–A–C(=O)–B–phenyl-R⁷]

| Name | R⁷ | A | B | Yield [%] | Melting range [°C] (recrystallized from) | Total formula (molar mass) |
|---|---|---|---|---|---|---|
| 23 | H | — | CH=CH | 60 | 109–111 (methanol) | $C_{17}H_{12}O_2$ (248.3) |
| 24 | 4-F | — | CH=CH | 65 | 114–116 (methanol) | $C_{17}H_{11}FO_2$ (266.3) |
| 25 | 4-Cl | — | CH=CH | 73 | 159–161 (ethylacetate) | $C_{17}H_{11}ClO_2O_2$ (282.7) |
| 26 | 4-NO₂ | — | CH=CH | 83 | 206–207 (methanol) | $C_{17}H_{11}NO_3$ (293.3) |
| 27 | 4-CH₃O | — | CH=CH | 84 | 122–125 (methanol) | $C_{18}H_{14}O_3$ (278.3) |
| 28 | 4-CF₃ | — | CH=CH | 63 | 175–176 (methanol) | $C_{18}H_{11}F_3O_2$ (316.3) |
| 29 | 4-NHSO₂CH₃ | — | CH=CH | 97 | 213–215 (methanol) | $C_{18}H_{15}NO_4S$ (341.4) |
| 30 | H | CH=CH | — | 75 | 90–92 (ethanol) | $C_{17}H_{12}O_2$ (248.3) |
| 31 | 3-NHSO₂CH₃ | CH=CH | — | 90 | 174–176 (ethanol) | $C_{18}H_{15}NO_4S$ (341.4) |
| 32 | 4-NHSO₂CH₃ | CH=CH | — | 87 | 203–206 (ethanol) | $C_{18}H_{15}NO_4S$ (341.4) |

EXAMPLE 3

1-(benzo[b]furan-2-yl)-3-phenylpropane-1-one 33

A 10% methanolic solution of ethenyl compound 23 is hydrogenated by means of 10% palladium/active carbon at a slight overpressure until the theoretical hydrogen take-up is reached, and filtered. The solution is then evaporated under vacuum. The compound thus obtained is recrystallized from 2-propanol.

Yield: 97%, white crystals

Melting range: 61°–63° C.

The compounds listed in Table 7 were prepared in accordance with these instructions. The substances thus obtained mostly are sufficiently pure. If required, they can be recrystallized from methanol or the like. The yields are between 43% and 80% of the theoretical quantity.

TABLE 7

[Structure: benzofuran-2-yl–A–C(=O)–B–phenyl-R⁷]

| Name | R⁷ | A | B | Yield [%] | Melting range [°C] (recrystallized from) | Total formula (molar mass) |
|---|---|---|---|---|---|---|
| 33 | H | — | CH₂—CH₂ | 97 | 61–63 (2-propanol) | $C_{17}H_{14}O_2$ (250.3) |
| 34 | 4-Cl | — | CH₂—CH₂ | 80 | 83–86 (methanol) | $C_{17}H_{13}ClO_2$ (284.8) |
| 35 | 4-OCH₃ | — | CH₂—CH₂ | 49 | 59–61 (ethanol) | $C_{18}H_{16}O_3$ (280.3) |
| 36 | 3-NHSO₂CH₃ | — | CH₂—CH₂ | 51 | 131–132 (2-propanol) | $C_{18}H_{17}NO_4S$ (343.3) |
| 37 | 3-NHSO₂CH₃ | CH₂—CH₂ | — | 43 | 137–139 (methanol) | $C_{18}H_{17}NO_4S$ (343.3) |
| 38 | 4-NHSO₂CH₃ | CH₂—CH₂ | — | 48 | 162–163 (ethanol) | $C_{18}H_{17}NO_4S$ (343.3) |

EXAMPLE 4

(E)- and (Z)-2-benzoylbenzo[b]furan amidinohydrazone hydrochloride 39 and 40

40 ml of ethanol and 8 ml of concentrated hydrochloric acid are poured over 7.7 g of 2-benzoylbenzo[b]furan and 5.1 g of aminoguanidine hydrochloride; the batch is heated under stirring in a reflux condenser for 5 hours. Subsequently, the solution is cooled down to 5° C., and the product is crystallized. It is filtered off by suction, and the first fraction is recrystallized from ethanol.

(E)-2-benzoylbenzo[b]furan amidinohydrazone hydrochloride 39; Yield: 41%. Colourless crystals (cf. Table 8).

After the above-mentioned compound is separated, a second fraction will crystallize from the mother liquor when stored in a refrigerator. This fraction is filtered off by suction and recrystallized from ethanol.

(Z)-2-benzoylbenzo[b]furan amidinohydrazone hydrochloride 40; Yield: 29%. Colourless crystals (cf. Table 8).

The compounds listed in Tables 8 to 16 are produced in a similar way. Most of them are isolated as mixtures of isomers.

TABLE 8

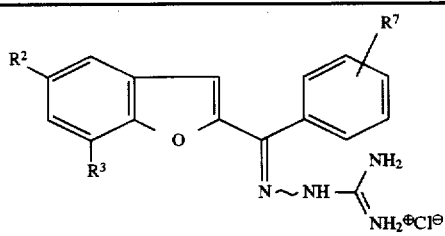

| Name | $R^2$ | $R^3$ | $R^7$ | Yield [%] | Melting range [°C] (recystallized from) | Total formula (molar mass) |
|---|---|---|---|---|---|---|
| 39 | H | H | H | 41 | 161–167 (ethanol) | $C_{16}H_{15}ClN_4O$ (314.8) |
| 40 | H | H | H | 29 | 207–208 (ethanol) | $C_{16}H_{15}ClN_4O$ (314.8) |
| 41 | H | H | 4-CH$_3$ | 63 | 252–255 (ethanol) | $C_{17}H_{17}ClN_4O$ (328.8) |
| 42 | H | H | 4-OCH$_3$ | 45 | 218–220 (ethanol) | $C_{17}H_{17}ClN_4O_2$ (344.8) |
| 43 | H | H | 4-CH$_3$SO$_2$NH | 96 | 307–310 (methanol) | $C_{17}H_{18}ClN_5O_3S \cdot H_2O$ (425.9) |
| 44 | H | H | 4-NH$_2$.HCl | 80 | 195–204 (methanol/ether) | $C_{16}H_{17}Cl_2N_5O$ (350.2) |
| 45 | H | H | 4-Br | 62 | 260–261 (methanol) | $C_{16}H_{14}BrClN_4O$ (393.7) |
| 46 | H | H | 4-Cl | 77 | 248–250 (methanol) | $C_{16}H_{14}Cl_2N_4O$ (349.2) |
| 47 | H | H | 4-NO$_2$ | 60 | 267–270 (methanol/HCl) | $C_{16}H_{14}ClN_5O_3$ (359.8) |
| 48 | H | H | 4-CN | 50 | from 250 (methanol/HCl) | $C_{17}H_{14}ClN_5O$ (339.8) |
| 49 | Br | H | 4-cyclo-C$_6$H$_{11}$ | 47 | 157–159 (methanol) | $C_{22}H_{24}BrClN_4O$ (475.8) |
| 50 | H | H | 3-NO$_2$ | 91 | 255–259 (methanol) | $C_{16}H_{14}ClN_5O_3$ (359.8) |
| 51 | Br | H | H | 53 | 276–279 (ethanol) | $C_{16}H_{14}BrClN_4O$ (393.7) |
| 52 | Br | H | 4-Cl | 33 | 184–188 (methanol) | $C_{16}H_{13}BrCl_2N_4O$ (428.1) |
| 53 | Br | H | 4-Br | 57 | 152–188 (methanol) | $C_{16}H_{13}Br_2ClN_4O$ (472.6) |
| 54 | Br | H | 4-CN | 60 | from 210 dec. (methanol/ether) | $C_{17}H_{13}BrClN_5O$ (418.7) |
| 55 | Br | H | 4-CH$_3$CONH | 68 | from 195 dec. (methanol) | $C_{18}H_{17}BrClN_5O_2$ (450.7) |
| 56 | NO$_2$ | H | H | 99 | 260–268 dec. (methanol) | $C_{16}H_{14}ClN_5O_3$ (359.8) |
| 57 | CH$_3$SO$_2$NH | H | H | 99 | 190–207 (methanol/ether) | $C_{17}H_{18}ClN_5O_3S$ (407.9) |
| 58 | Br | H | 4-NO$_2$ | 66 | 181–185 (methanol) | $C_{16}H_{13}BrClN_5O_3$ (438.7) |
| 59 | NO$_2$ | H | 4-CN | 71 | 308–316 (methanol) | $C_{17}H_{13}ClN_6O_3$ (384.8) |
| 60 | CN | H | H | 35 | from 163 (methanol) | $C_{17}H_{14}ClN_5O$ (339.8) |
| 61 | Br | H | 3-NO$_2$ | 44 | 154–158 (methanol) | $C_{16}H_{13}BrClN_5O_3$ (438.7) |
| 62 | I | I | H | 57 | from 276 dec. | $C_{16}H_{13}ClI_2N_4O$ |

TABLE 8-continued

| Name | R² | R³ | R⁷ | Yield [%] | Melting range [°C] (recystallized from) | Total formula (molar mass) |
|---|---|---|---|---|---|---|
| | | | | | (methanol) | (566.6) |
| 63 | Br | H | 4-CH₃ | 21 | 260–263 (ethanol) | $C_{17}H_{16}BrClN_4O$ (407.7) |
| 64 | Br | Br | H | 45 | 243–245 (ethanol) | $C_{16}H_{13}Br_2ClN_4O$ (472.6) |
| 65 | H | H | 4-F | 72 | 236–246 (methanol) | $C_{16}H_{14}ClFN_4O$ (332.8) |
| 66 | H | H | 3,4-(CH₃O)₂ | 95 | 144–158 (methanol) | $C_{18}H_{19}ClN_4O_3$ (374.8) |
| 67 | H | H | 2-F | 70 | 207–235 (methanol) | $C_{16}H_{14}ClFN_4O$ (332.8) |
| 68 | H | H | 4-OCF₃ | 5 | 119–125 (methanol) | $C_{17}H_{14}ClF_3N_4O_2$ (398.8) |
| 69 | H | H | 4-CF₃ | 92 | from 220 dec. (methanol) | $C_{17}H_{14}ClF_3N_4O$ (382.8) |
| 70 | H | H | 3-OCF₃ | 95 | from 205 dec. (methanol) | $C_{17}H_{14}ClF_3N_4O_2$ (398.8) |
| 71 | H | H | 3-CF₃ | 82 | from 233 dec. (methanol) | $C_{17}H_{14}ClF_3N_4O$ (382.8) |
| 72 | I | I | 4-CF₃ | 85 | from 267 dec. (methanol) | $C_{17}H_{12}ClF_3I_2N_4O$ (634.6) |
| 73 | NO₂ | H | 3-OCF₃ | 79 | from 245 dec. (methanol) | $C_{17}H_{13}ClF_3N_5O_4$ (443.8) |
| 74 | Cl | H | 4-CF₃ | 96 | from 240 dec. (methanol) | $C_{17}H_{13}Cl_2F_3N_4O$ (417.2) |
| 75 | NO₂ | H | 4-CF₃ | 88 | from 295 dec. (methanol) | $C_{17}H_{13}ClF_3N_5O_3$ (427.8) |
| 76 | NO₂ | H | 4-OCF₃ | 88 | 293–301 dec. (methanol) | $C_{17}H_{13}ClF_3N_5O_4$ (443.8) |
| 77 | NO₂ | H | 3-CF₃ | 84 | from 124 dec. (methanol) | $C_{17}H_{13}ClF_3N_5O_3$ (427.8) |
| 78 | Cl | H | H | 94 | 225–244 dec. (methanol) | $C_{16}H_{14}Cl_2N_4O$ (349.2) |
| 79 | H | OCH₃ | H | 37 | 240–255 (methanol) | $C_{17}H_{17}ClN_4O_2$ (498.6) |
| 80 | CH₃SO₂NH | H | 3-CF₃ | 64 | 256–264 dec. (methanol) | $C_{18}H_{17}ClF_3N_5O_3S$ (475.8) |

TABLE 9

| Name | R⁷ | Yield [%] | Melting range [°C] (methanol/HCl) | Total formula (molar mass) |
|---|---|---|---|---|
| 81 | 4-CH₃SO₂NH | 60 | 204–206 | $C_{19}H_{20}ClN_5O_3S$ (433.9) |
| 82 | H | 71 | 209–210 | $C_{18}H_{17}ClN_4O$ (340.8) |
| 83 | 4-F | 60 | 226–233 | $C_{18}H_{16}ClFN_4O$ (358.8) |
| 84 | 4-Cl | 90 | 230–235 | $C_{18}H_{16}Cl_2N_4O$ (375.3) |
| 85 | 4-NO₂ | 100 | 160–170 247–252* | $C_{18}H_{16}ClN_5O_3 \cdot H_2O$ (403.8) |
| 86 | 4-OCH₃ | 65 | 205–214 | $C_{19}H_{19}ClN_4O_2$ (370.8) |
| 87 | 3-Br | 60 | 225–231 | $C_{18}H_{16}BrClN_4O$ (419.7) |

TABLE 9-continued

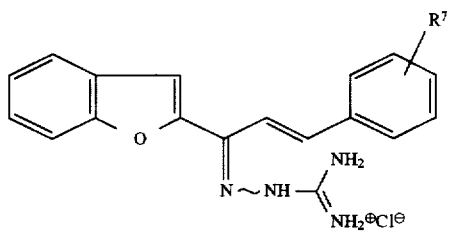

| Name | R⁷ | Yield [%] | Melting range [°C.] (methanol/HCl) | Total formula (molar mass) |
|---|---|---|---|---|
| 88 | 3-NO₂ | 90 | 271–273 | $C_{18}H_{16}ClN_5O_3$ (385.8) |
| 89 | 4-CF₃ | 65 | 215–225 | $C_{19}H_{16}ClF_3N_4O$ (408.8) |

*isomeric compound!

TABLE 10

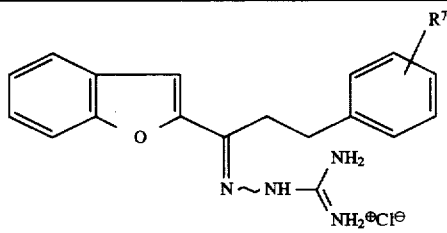

| Name | R⁷ | Yield [%] | Melting range [°C.] (recrystallized from) | Total formula (molar mass) |
|---|---|---|---|---|
| 90 | H | 70 | 251–260 (methanol) | $C_{18}H_{19}ClN_4O$ (342.8) |
| 91 | 4-Cl | 95 | 243–244 (methanol) | $C_{18}H_{18}Cl_2N_4O$ (377.3) |
| 92 | 4-OCH₃ | 95 | 206–210 (methanol) | $C_{19}H_{21}ClN_4O_2$ (372.9) |
| 93 | 3-NHSO₂CH₃ | 92 | 205–210 (methanol/ether) | $C_{19}H_{22}ClN_5O_3S$ (435.9) |

TABLE 11

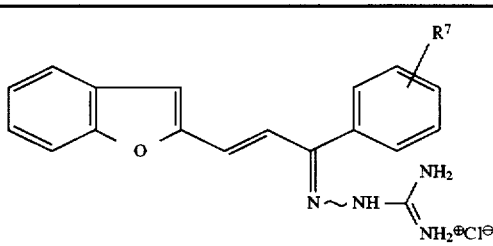

| Name | R⁷ | Yield [%] | Melting range [°C.] (ethanol/ether) | Total formula (molar mass) |
|---|---|---|---|---|
| 94 | H | 63 | 227–235 | $C_{18}H_{17}ClN_4O$ (340.1) |
| 95 | 3-CH₃SO₂NH | 30 | 272–276 | $C_{19}H_{20}ClN_5O_3S$ (433.9) |
| 96 | 4-CH₃SO₂NH | 11 | 243–249 | $C_{19}H_{20}ClN_5O_3S$ (433.9) |

TABLE 12

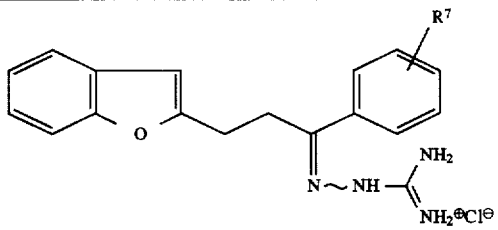

| Name | R⁷ | Yield [%] | Melting range [°C.] (methanol/ether) | Total formula (molar mass) |
|---|---|---|---|---|
| 97 | 3-NHSO₂CH₃ | 70 | 220–224 | $C_{19}H_{22}ClN_5O_3S$ (435.9) |
| 98 | 4-NHSO₂CH₃ | 82 | from 218 | $C_{19}H_{22}ClN_5O_3S$ (435.9) |

TABLE 13

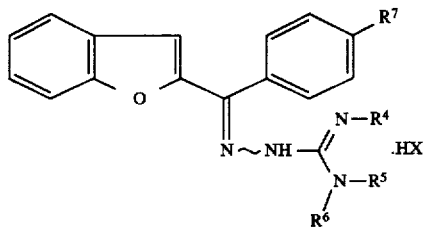

| Name | R⁴ | R⁵ | R⁶ | R⁷ | X | Yield [%] | Melting range [°C.] (recryst. from) | Total formula (molar mass) |
|---|---|---|---|---|---|---|---|---|
| 99 | H | CH₃ | CH₃ | H | Cl | 57 | from 190 dec. (methanol/ether) | $C_{18}H_{19}ClN_4O \cdot CH_3OH$ (342.9) |
| 100 | H | C₆H₅ | H | H | NO₃ | 60 | 148–155 (methanol) | $C_{22}H_{19}N_5O_4$ (417.4) |
| 101 | H | C₆H₅ | H | CH₃SO₂NH | NO₃ | 90 | 175–185 (methanol/HNO₃) | $C_{23}H_{22}N_6O_6$ (510.5) |
| 102 | H | —(CH₂)₅— | | H | Cl | 60 | from 130 (methanol/ether) | $C_{21}H_{23}ClN_4O$ (382.9) |

TABLE 13-continued

[Structure: benzofuran-2-yl connected to C(=N~NH-C(=N-R⁴)(N(R⁵)R⁶))-phenyl-R⁷ · HX]

| Name | R⁴ | R⁵ | R⁶ | R⁷ | X | Yield [%] | Melting range [°C.] (recryst. from) | Total formula (molar mass) |
|---|---|---|---|---|---|---|---|---|
| 103 | H | CH(CH₃)₂ | H | H | I | 55 | 153–162 (methanol/ether) | C₁₉H₂₁IN₄O (448.3) |

TABLE 14

[Structure: R²,R³-substituted benzofuran-2-yl-C(R)=N~NH-C(NH₂)=NH₂⁺ Cl⁻]

| Name | R | R² | R³ | Yield [%] | Melting range [°C.] (recrystallized from) | Total formula (molar mass) |
|---|---|---|---|---|---|---|
| 104 | benzofuran-2-yl | H | H | 78 | 261–264 (n-propanol) | C₁₈H₁₅ClN₄O₂ (354.8) |
| 105 | naphthalen-2-yl | Br | H | 38 | from 148 dec. (methanol/HCl) | C₂₀H₁₆BrClN₄O (443.7) |
| 106 | benzofuran-2-yl | Br | H | 95 | from 150 dec. (methanol) | C₁₈H₁₃BrClN₄O₂ (432.7) |
| 107 | —(CH₂)₂—N(CH₃)₂·HCl | H | H | 58 | 223–234 (methanol/ether) | C₁₄H₂₁Cl₂N₅O (346.3) |
| 108 | —CH₃ | H | H | 80 | from 183 (methanol/ether) | C₁₁H₁₃ClN₄O (252.7) |
| 109 | benzofuran-2-yl | Br | Br | 85 | 157–165 dec. (methanol) | C₁₈H₁₃Br₂ClN₄O₂ (512.6) |
| 110 | —C₂H₅ | Br | H | 90 | from 202 (methanol) | C₁₂H₁₄BrClN₄O (345.6) |
| 111 | —CH₂—C₆H₅ | H | H | 96 | from 243 (methanol) | C₁₇H₁₇ClN₄O (328.8) |
| 112 | —CH₂—C₆H₅ | Cl | H | 80 | 260–270 (methanol) | C₁₇H₁₆Cl₂N₄O (363.2) |
| 113 | —CH₂—C₆H₅ | Br | H | 90 | from 202 (methanol) | C₁₇H₁₆BrClN₄O (407.7) |
| 114 | —C₂H₅ | H | H | 66 | 80–85 (methanol) | C₁₂H₁₅ClN₄O (266.7) |

TABLE 15

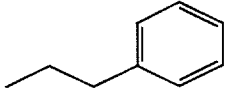

| Name | R² | R³ | Yield [%] | Melting range [°C] (methanol/ether) | Total formula (molar mass) |
|---|---|---|---|---|---|
| 115 | H | H | 60 | from 178 | $C_{18}H_{17}ClN_4O$ (340.8) |
| 116 | Br | Br | 45 | 277–285 dec. | $C_{18}H_{15}Br_2ClN_4O$ (498.6) |

TABLE 16

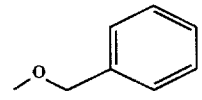

| Name | R¹ | R² | R³ | Yield [%] | Melting range [°C] (recrystallized from) | Total formula (molar mass) |
|---|---|---|---|---|---|---|
| 117 | $NH_2 \cdot H_2O$ | H | H | 40 | 165–173 dec. (water) | $C_{18}H_{16}ClN_5O_2$ (347.8) |
| 118 | $CH_3$ | H | H | 15 | 141–145 (methanol/ether) | $C_{17}H_{17}ClN_4O$ (328.8) |
| 119 | 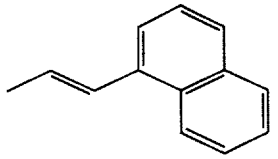 | 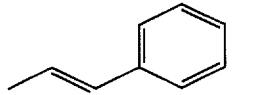 | H | 18 | 217–226 dec. (ethanol) | $C_{31}H_{29}ClN_4O_2$ (525.0) |
| 120 | $CH_3$ | H | 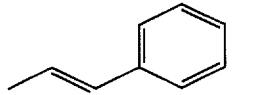 | 68 | 268–274 (ethanol) | $C_{24}H_{23}ClN_4O_2$ (434.9) |
| 121 | (1-propenyl-naphthyl) | H | H | 31 | from 173 (ethanol) | $C_{25}H_{23}ClN_4O$ (467.0) |
| 122 | (1-propenyl-phenyl) | H | 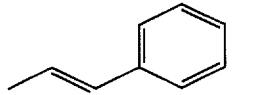 | 30 | 217–226 (ethanol) | $C_{31}H_{27}ClN_4O_2$ (523.0) |
| 123 | $CH_3$ | $NO_2$ | H | 95 | from 178 dec. (methanol) | $C_{17}H_{16}ClN_5O_3$ (373.8) |

EXAMPLE 5

2-benzoylbenzo[b]furan-N³-benzoyl amidinohydrazone hydrochloride 124

3.0 g (Z/E)-2-benzoylbenzo[b]furan amidinohydrazone hydrochloride 39/40 are dissolved under gentle warming in 300 ml of water, and the solution is alkalinized after cooling with a 5% solution of potassium hydroxide. The precipitate is filtered off by suction, washed with water, and dried. 0.85 ml of benzoylchloride dissolved in 8 ml of dry dioxane are added by dropping and under stirring to an ice-cooled solution of 1.4 g of 2-benzoylbenzo[b]furan amidinohydrazone, 0.85 ml of diiso-propyl-ethyl-amine and 1.2 g of 4-(N,N-dimethylamino)pyridine in 14 ml of dry pyridine. The orange solution is stirred for another 2 hours. The batch is then poured into iced water, the yellow precipitate is filtered off by suction, washed with water, and dried. The crystal powder obtained in this way is treated with 20 ml of methanol saturated with hydrogen chloride. Then the solvent is carefully distilled off under vacuum. The substance is dried under high vacuum by codistillation with dry toluene. The substance is purified by dissolving it in chloroform/methanol and mixing it for fractional precipitation with ethyl acetate and then with ether until it is strongly clouded. The precipitate is filtered off by suction, washed in a small quantity of ether, and dried.

The compounds listed in Table 17 are obtained in a similar way.

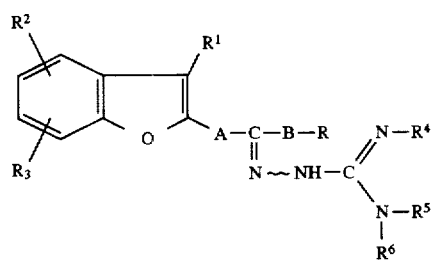

wherein

R is a linear or branched alkyl or dialkyl aminoethyl group containing up to 6 C atoms, or one of the residues

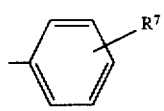

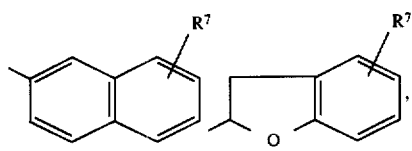

wherein $R^7$ represents a hydrogen atom, a halogen atom, a linear or branched alkyl or alkoxy group containing up to 6 C atoms, an aralkyl or aralkoxy group containing up to 9 C atoms, a cyano, nitro, methane sulfonamido, acetylamino, trifluoromethyl,

TABLE 17

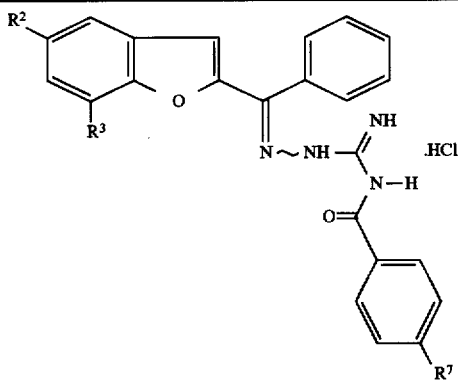

| Name | $R^2$ | $R^3$ | $R^7$ | Yield [%] | Melting range [°C.] (recrystallized from) | Total formula (molar mass) |
|---|---|---|---|---|---|---|
| 124 | H | H | H | 75 | 105–108 (methanol/ether) | $C_{23}H_{19}ClN_4O_2$ (418.9) |
| 125 | H | H | $CH_3SO_2NH$ | 43 | 170–182 (ether) | $C_{24}H_{22}ClN_5O_4S$ (512.0) |
| 126 | H | H | $NO_2$ | 30 | from 165 dec. (methanol) | $C_{23}H_{18}ClN_5O_4$ (463.9) |
| 127 | Br | H | H | 55 | 185–195 dec. (methanol/ether) | $C_{23}H_{18}BrClN_4O_2$ (497.8) |
| 128 | Br | Br | H | 42 | 248–254 dec. (methanol/ether) | $C_{23}H_{17}Br_2ClN_4O_2$ (576.7) |

We claim:

1. An amidinohydrazone of the general formula I, or a mixture thereof

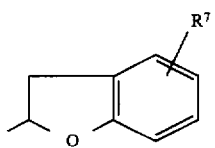

for any compound when A and B are not present.

A and B independently represent either $(CH_2)_n$ or $(CH=CH)_m$, with n=0, 1 or 2 and m=0 or 1, provided that m or n is not zero for A when both B is $(CH=CH)_1$ and $R^4$ with $R_5$ forms a heterocyclic ring.

$R^1$ is a hydrogen atom, an amino, a linear or branched alkyl residue containing up to 6 C atoms, an aralkyl residue containing up to 9 C atoms, a methane sulfonamido, acetylamino, cyano, (1H-imidazole-1-yl) residue, or one of the residues

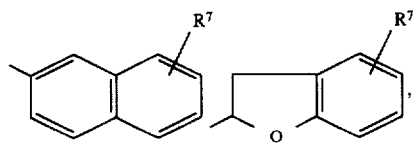

wherein $R^7$ is as defined above, $R^2$ and $R^3$ independently represent a hydrogen atom, a linear or branched alkyl or alkoxy group containing up to 6 C atoms, an aralkyl or aralkoxy group containing up to 9 C atoms, a halogen atom, a cyano, nitro, methane sulfonamido, acetylamino, trifluoromethyl, trifluoromethoxy, amino or (1H-imidazole-1-yl) group $R^4$ is a hydrogen atom, a linear or branched alkyl group containing up to 6 C atoms, an aralkyl group containing up to 9 C atoms, or one of the residues,

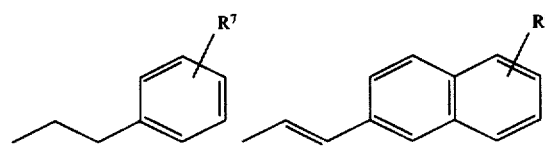

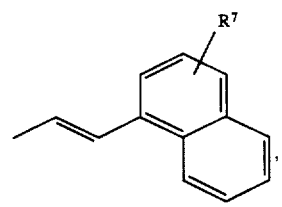

wherein $R^7$ is as defined above, $R^5$ and $R^6$ independently represent a hydrogen atom, a linear or branched alkyl, alkanoyl, or alkylsulfonyl residue containing up to 6 C atoms, an aralkyl residue containing up to 9 C atoms, a (4-methylphenyl) sulfonyl, a trifluoroacetyl, or one of the residues

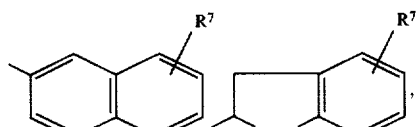

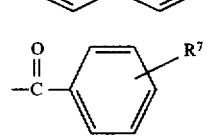

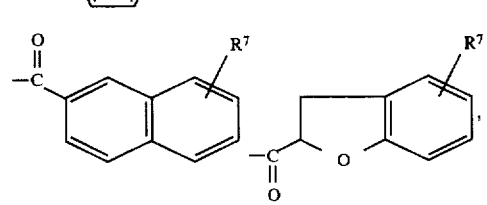

wherein $R^7$ is as defined above, or $R^4$ and $R^5$ jointly represent an ethylene or propylene fragment, or $R^5$ and $R^6$, together with the N atom, represent a piperidino, morpholino, or piperazino residue, and wherein the zig-zagged bond in the structure of amidinohydrazone indicates that the compound is present in the form of the (Z) or (E) isomer, or mixtures of isomers, or a salt formed with one or several physiologically tolerable acids.

2. The amidinohydrazone of claim 1 wherein said physiologically tolerable acids are selected from the group consisting of mineral acids, linear or branched alkanoic or alkanoic acids or alkylsulfonic acids containing up to 6 C atoms or arenocarboxylic acids, the organic acids optionally carrying additional halogen, amino, dialkylamino (containing up to 6 C atoms), hydroxy, and carboxy residues.

3. Method for producing the amidinohydrazones according to claim 1 comprising fusing ketones derived from benzo[b]furan of the general formula II,

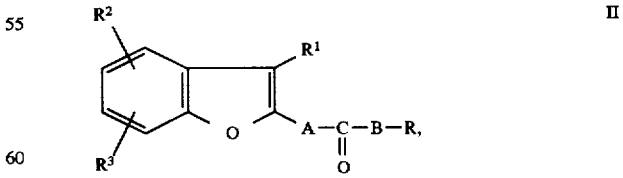

in which the residues R, $R^1$, $R^2$, and $R^3$ are as defined in claim 1, by heating said ketones in a short-chain alkanol in the presence of mineral or sulfonic acids with an aminoguanidine of the general formula III,

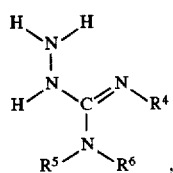 III in which the residues $R^4$, $R^5$ and $R^6$ are as defined in claim 1, said aminoguanidine optionally being present in the form of a physiologically tolerable salt formed with an inorganic or organic acid, and producing a physiologically tolerable salt by one of
a. releasing the base from the compounds thus obtained and reacting said base with a physiologically tolerable acid; and
b. reacting the compounds thus obtained in a suitable solvent and in the presence of auxiliary bases with acyl halogenides of the formulae

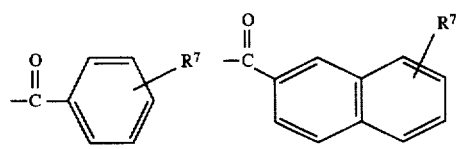

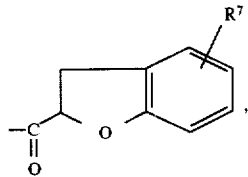

in which $R^7$ is as defined in claim 1 and X represents a halogen atom, and by reacting the N acyl derivatives obtained with a physiologically tolerable acid.

4. The method of claim 3 wherein said physiologically tolerable acids are selected from the group consisting of mineral acids, linear or branched alkanoic or alkanoic acids or alkylsulfonic acids containing up to 6 C atoms or arenocarboxylic acids, the organic acids optionally carrying additional halogen, amino, dialkylamino (containing up to 6 C atoms), hydroxy, and carboxy residues.

5. A pharmaceutical comprising at least one compound according to claim 1 and, optionally, other active ingredients as well as pharmaceutically acceptable substrates and adjuvants.

* * * * *